United States Patent [19]
Lager

[11] Patent Number: 5,217,477
[45] Date of Patent: Jun. 8, 1993

[54] DUAL WIDTH SURGICAL KNIFE

[75] Inventor: Paul H. Lager, Fort Worth, Tex.

[73] Assignee: Alcon Surgical, Inc., Fort Worth, Tex.

[21] Appl. No.: 833,196

[22] Filed: Feb. 10, 1992

[51] Int. Cl.$^5$ .............................................. A61B 17/32
[52] U.S. Cl. ................................... 606/167; 606/166; 30/355
[58] Field of Search ........................ 606/166, 167, 170; 30/353, 355, 337

[56] References Cited

U.S. PATENT DOCUMENTS

| | | | |
|---|---|---|---|
| 1,527,561 | 2/1925 | Klum | 30/355 |
| 3,367,335 | 2/1968 | Ward et al. | 606/167 |
| 4,688,570 | 8/1987 | Kramer et al. | 606/166 |
| 5,080,111 | 1/1992 | Pallin . | |

FOREIGN PATENT DOCUMENTS 3624243  1/1988  Fed. Rep. of Germany ...... 606/167

OTHER PUBLICATIONS

An advertisement of a dual-width surgical knife manufactured by MSP that appeared in the Jan. 15, 1992 issue of *Ocular Surgery News* at page 55.

Primary Examiner—C. Fred Rosenbaum
Assistant Examiner—William W. Lewis
Attorney, Agent, or Firm—Jeffrey S. Schira

[57] ABSTRACT

A surgical knife having a handle and a blade with a first generally V-shaped portion for cutting an incision having a first width of approximately 3.2 millimeters and a second generally arcuate portion for widening the incision to a second width of approximately 5.2 millimeters.

8 Claims, 2 Drawing Sheets

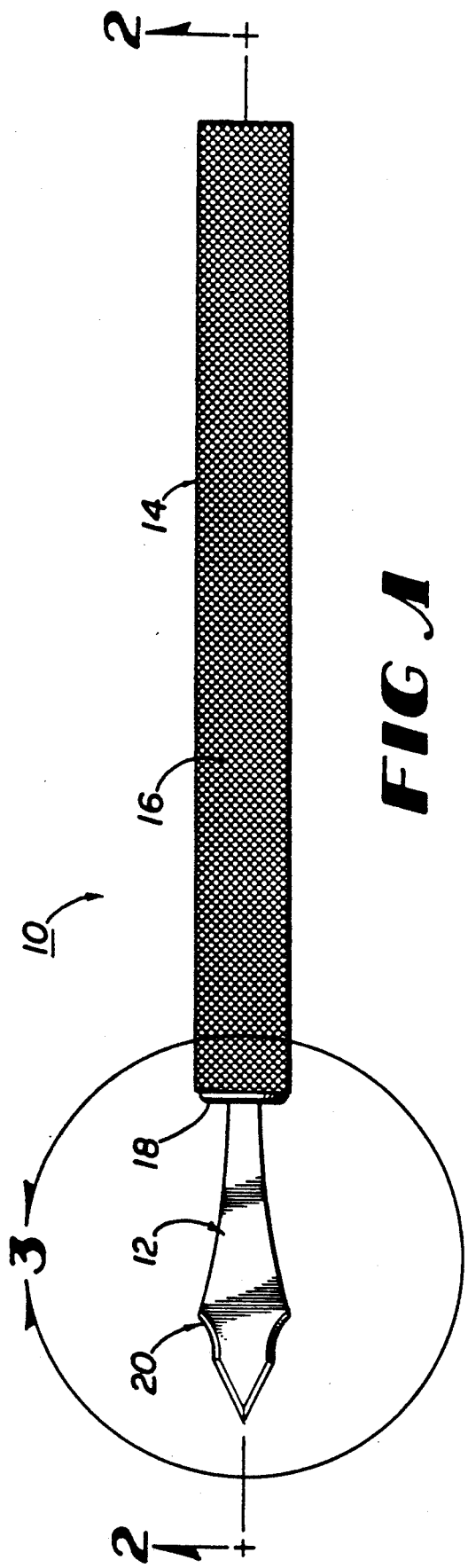
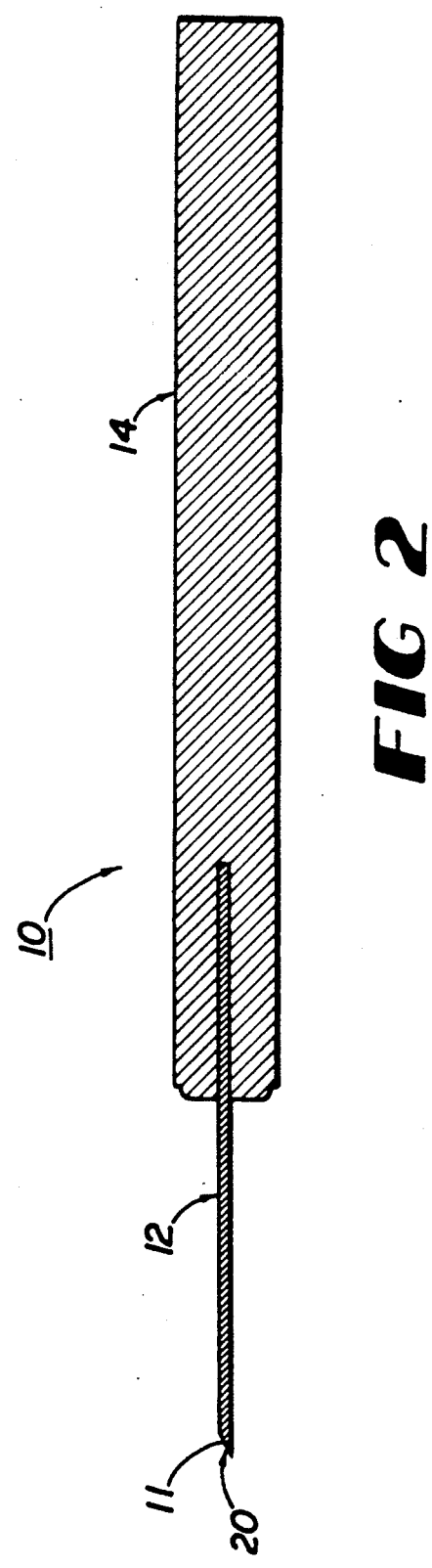

… …

DUAL WIDTH SURGICAL KNIFE

BACKGROUND OF THE INVENTION

The present invention relates to surgical knives and particularly to knives used in ophthalmic surgery.

For many years, the predominant method of treating a diseased lens is to remove the diseased lens and replace it with an intraocular lens ("IOL"). Two surgical procedures are preferred for removing the diseased lens: extracapsular cataract extraction and phacoemulsification. Extracapsular cataract extraction involves removing the lens in a relatively intact condition by use of a vectus or similar surgical instrument. Phacoemulsification involves contacting the lens with the vibrating cutting tip of an ultrasonically driven surgical handpiece to emulsify the lens, thereby allowing the emulsified lens to be aspirated from the eye. Although extracapsular cataract extraction has been the preferred surgical technique, phacoemulsification has become increasingly popular, in part because the cutting tip of the ultrasonic handpiece requires only a relatively small (approximately 3 millimeter) tunnel incision.

A typical IOL comprises an artificial lens ("optic") and at least one support member ("haptic") for positioning the IOL within the capsular bag. The optic may be formed from any of a number of different materials, including polymethylmethacrylate (PMMA), polycarbonate and acrylics, and it may be hard, relatively flexible or even fully deformable so that the IOL can be rolled or folded prior to insertion. The haptics generally are made from some resilient material, such as polypropylene or PMMA and are generally attached to the optic at the 9 o'clock and 3 o'clock positions. IOL's may be characterized as either "one-piece" or "multi-piece." With one-piece IOL's, the haptic and the optic are formed integrally as a blank and the IOL is then milled or lathed to the desired shape and configuration. The multi-piece IOL's are formed either by attaching the haptic to a pre-formed optic or by molding the optic around the proximal end of the haptic.

The diameter of the optic varies depending on the design of the IOL, but an optic diameter of around 5 millimeters (mm) is most common. Although some IOL's are made from a foldable material, allowing the IOL to be inserted through the typical 3 mm incision used with phacoemulsification, in general, the incision must be enlarged after the aspiration of the cataractous lens to allow the IOL to be implanted. Prior to the present invention, surgeons typically used two separate surgical knives, one with a blade width of approximately 3.2 mm for making the initial incision, and a second knife with a blade width of approximately 5.2 mm for widening the initial incision to permit IOL insertion. While the use of two separate knives works well, it results in added expense and time in purchasing, inventorying and, in the case of reusable knives, sterilizing two different knives.

Accordingly, a need continues to exist for a surgical knife that will precisely cut both the initial small incision needed for the ultrasonic cutting tip and the wider IOL insertion incision used in phacoemulsification.

BRIEF SUMMARY OF THE INVENTION

The present invention improves upon prior art surgical knives by providing a knife with a dual width blade. The first portion of the blade contains a sharp cutting point that, at its widest point, is approximately 3.2 mm wide, the incision width most commonly used with phacoemulsification cutting tips. The blade width then flares gently along a generally arcuate path to approximately 5.2 mm, the incision width preferred by surgeons for small incision, PMMA IOL insertion. The dual widths of the surgical knife of the present invention allow the surgeon to make both required incisions with a single knife, thereby eliminating the use of two separate knives.

Accordingly, one objective of the present invention is to provide a surgical knife capable of making incisions of varying widths.

Another objective of the present invention is to provide a surgical knife capable of making both incision widths typically needed during cataract surgery using phacoemulsification.

Another objective of the present invention is to provide a surgical knife having a scalloped, dual-width blade.

These and other objectives and advantages of the present invention will become apparent from the detailed description, drawings and claims that follow.

BRIEF DESCRIPTION OF THE DRAWING

FIG. 1 is a plan view of the surgical knife of the present invention.

FIG. 2 is a cross-sectional view of the intraocular lens illustrated in FIG. 1 taken along line 2—2.

DETAILED DESCRIPTION OF THE INVENTION

Figure 3:
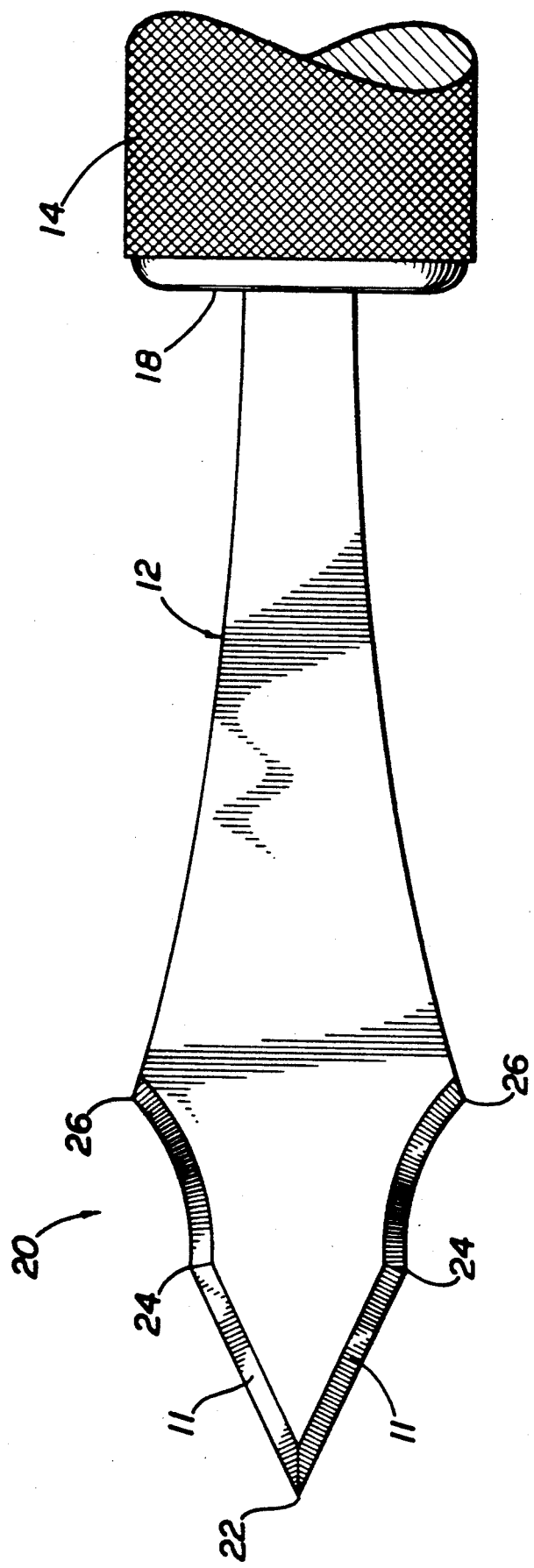
FIG. 3 is an enlarged plan view of the surgical knife of the present invention taken at circle 3 on FIG. 1.

As can be seen in FIGS. 1, 2 and 3, surgical knife 10 of the present invention includes a blade 12 and a handle 14. Knife 10 may be either reusable or disposable. If knife 10 is to be reusable, blade 12 may be made of any suitable material such as stainless steel or titanium and handle 14 may be made from stainless steel, titanium, or aluminum. If knife 10 is to be disposable, handle 14 also may be made of suitable thermoplastic, fiberglass or composite material. Handle 14 is preferably cylindrical, although other cross-sectional shapes may also be used, and contains knurling 16 or other suitable roughening to make handle 14 more positive to grip.

As can be seen in FIG. 2, blade 12 preferably has a thin cross-section and a sharpened edge 11, is between 17 and 19 mm long, with 18 mm being preferred, and is attached to end 18 of handle 14 by any conventional means. As can best be seen in FIG. 3, cutting end 20 of blade 12 opposite handle end 18 is generally V-shaped from tip 22 to reference points 24 so that the width of cutting end 20 of blade 12 at reference points 24 is approximately between 2.8 and 3.5 mm, with 3.2 mm being preferred. The length of cutting end 20 between tip 22 and reference points 24 is approximately between 3.0 and 4.0 mm, with 3.5 mm being preferred. Between reference points 24 and terminal points 26, cutting end 20 of blade 12 widens along a generally arcuate path to approximately between 3.5 and 5.4 mm, with 5.2 mm being preferred. The use of a scalloped design between reference points 24 and terminal points 26 forces edge 11 to slice across the tissue to be cut rather than pushed against the tissue, allowing for more control and even, smooth cutting. The radius of the arcuate path is approximately between 5.5 mm and 7.5 mm and the length of cutting end 20 of blade 12 between reference points 24 and terminal points 26 is approximately between 2.0 and 3.0 mm, with 2.5 mm being preferred.

In use, the surgeon pushes tip 22 of knife 10 against and pierces the tissue to be cut. The surgeon continues to push tip 22 against the tissue until cutting end 20 is suitably inserted into the tissue up to reference points 24 and removes knife 10. The phacoemulsification of the cataract is performed through this relatively small incision. Once phacoemulsification is complete, the surgeon fully inserts cutting end 20 of knife 10 into the incision, widening the incision to the width of blade 12 at terminal points 26, the widest part of blade 12 and removes knife 10. The IOL (not shown) can now be inserted.

This description is given for purposes of illustration and explanation. It will be obvious to those skilled in the relevant art that modifications may be made to the invention as described herein without departing from its scope or spirit.

I claim:

1. A surgical knife, comprising:
   a. a handle; and
   b. a flat blade having a sharp point, at least a first generally V-shaped portion having straight edges for cutting an incision having a first width of approximately between 3.0 millimeters and 3.4 millimeters and, in tandem with the V-shaped portion, a second generally inwardly arcuate portion for widening the incision to a second width of approximately between 5.0 millimeters and 5.4 millimeters.

2. The surgical knife of claim 1 wherein the first width is approximately 3.2 millimeters.

3. The surgical knife of claim 1 wherein the second width is approximately 5.2 millimeters.

4. The surgical knife of claim 1 wherein the blade comprises stainless steel.

5. The surgical knife of claim 1 wherein the blade comprises titanium.

6. The surgical knife of claim 1 wherein the handle comprises stainless steel.

7. The surgical knife of claim 1 wherein the handle comprises thermoplastic.

8. The surgical knife of claim 1 wherein the handle comprises aluminum.

* * * * *